US010420605B2

(12) United States Patent
Rankin et al.

(10) Patent No.: US 10,420,605 B2
(45) Date of Patent: Sep. 24, 2019

(54) ABLATION PROBE WITH FLUID-BASED ACOUSTIC COUPLING FOR ULTRASONIC TISSUE IMAGING

(71) Applicants: Koninklijke Philips N.V., Eindhoven (NL); Boston Scientific Scimed Inc., Maple Grove, MN (US)

(72) Inventors: Darrell L. Rankin, Milpitas, MN (US); Josef V. Koblish, Sunnyvale, CA (US); Szabolcs Deladi, Veldhoven (NL)

(73) Assignees: Koninklijke Philips N.V., Eindhoven (NL); Boston Scientific Scimed Inc., Maple Grove, MN (US)

( * ) Notice: Subject to any disclaimer, the term of this patent is extended or adjusted under 35 U.S.C. 154(b) by 1282 days.

(21) Appl. No.: 14/603,173

(22) Filed: Jan. 22, 2015

(65) Prior Publication Data

US 2015/0133920 A1 May 14, 2015

Related U.S. Application Data

(62) Division of application No. 13/735,358, filed on Jan. 7, 2013, now Pat. No. 8,945,015.
(Continued)

(51) Int. Cl.
*A61B 18/14* (2006.01)
*A61B 8/12* (2006.01)
(Continued)

(52) U.S. Cl.
CPC ........ *A61B 18/1492* (2013.01); *A61B 5/0044* (2013.01); *A61B 8/12* (2013.01);
(Continued)

(58) Field of Classification Search
CPC ........ A61B 17/320068; A61B 18/1206; A61B 18/1492; A61B 2017/00243;
(Continued)

(56) References Cited

U.S. PATENT DOCUMENTS 3,773,401 A  11/1973  Douklias et al.
4,466,443 A  8/1984  Utsugi
(Continued)

FOREIGN PATENT DOCUMENTS

CA  2682055 A1  10/2008
CA  2846053 A1  3/2013
(Continued)

OTHER PUBLICATIONS

Goldberg, S. Nahum et al., "Variables Affecting Proper System Grounding for Radiofrequency Ablation in an Animal Model", JVIR, vol. 11, No. 8, Sep. 2000, pp. 1069-1075.
(Continued)

*Primary Examiner* — Amanda Lauritzen Moher
(74) *Attorney, Agent, or Firm* — Faegre Baker Daniels LLP

(57) ABSTRACT

Devices and systems for ultrasonically imaging tissue and performing ablation therapy are disclosed. An ablation probe for treating and imaging body tissue includes an ablation electrode tip with a number of acoustic openings and a plurality of ultrasonic imaging sensors disposed within an interior lumen of the tip. The ultrasonic imaging sensors are supported within the interior lumen via an insert equipped with a number of recesses that receive the ultrasonic imaging sensors. An acoustically transparent shell disposed between the ultrasonic imaging sensors and the acoustic openings forms a fluid channel in the acoustic pathway of the sensors. During an ablation procedure, cooling fluid from an external fluid source is delivered through the fluid channel, providing an acoustic coupling effect between the ultrasonic imaging sensors and the surrounding body tissue.

17 Claims, 4 Drawing Sheets

Related U.S. Application Data

(60) Provisional application No. 61/592,908, filed on Jan. 31, 2012.

(51) Int. Cl.

| | | |
|---|---|---|
| *A61B 8/00* | (2006.01) | |
| *A61B 8/08* | (2006.01) | |
| *A61B 18/12* | (2006.01) | |
| *A61M 5/00* | (2006.01) | |
| *A61N 7/00* | (2006.01) | |
| *A61B 17/32* | (2006.01) | |
| *A61B 5/00* | (2006.01) | |
| *A61B 17/00* | (2006.01) | |
| *A61H 23/02* | (2006.01) | |
| *A61B 17/02* | (2006.01) | |
| *A61B 18/00* | (2006.01) | |
| *A61B 90/00* | (2016.01) | |

(52) U.S. Cl.
CPC ............... *A61B 8/44* (2013.01); *A61B 8/445* (2013.01); *A61B 8/4444* (2013.01); *A61B 8/4477* (2013.01); *A61B 8/4494* (2013.01); *A61B 8/5207* (2013.01); *A61B 8/54* (2013.01); *A61B 17/320068* (2013.01); *A61B 18/1206* (2013.01); *A61M 5/00* (2013.01); *A61N 7/00* (2013.01); *A61B 5/0084* (2013.01); *A61B 5/6852* (2013.01); *A61B 5/6869* (2013.01); *A61B 8/0883* (2013.01); *A61B 8/4254* (2013.01); *A61B 8/4281* (2013.01); *A61B 2017/00243* (2013.01); *A61B 2017/0237* (2013.01); *A61B 2018/00029* (2013.01); *A61B 2090/378* (2016.02); *A61B 2090/3782* (2016.02); *A61H 23/0245* (2013.01); *A61N 2007/0004* (2013.01); *A61N 2007/0043* (2013.01); *A61N 2007/0078* (2013.01); *A61N 2007/0082* (2013.01)

(58) Field of Classification Search
CPC .. A61B 2017/0237; A61B 2018/00029; A61B 2090/378; A61B 2090/3782; A61B 5/0044; A61B 5/0084; A61B 5/6852; A61B 5/6869; A61B 8/0883
See application file for complete search history.

(56) References Cited

U.S. PATENT DOCUMENTS

| | | |
|---|---|---|
| 4,602,624 A | 7/1986 | Naples et al. |
| 4,633,882 A | 1/1987 | Matsuo et al. |
| 4,732,149 A | 3/1988 | Sutter |
| 4,763,660 A | 8/1988 | Kroll et al. |
| 4,966,145 A | 10/1990 | Kikumoto et al. |
| 5,019,076 A | 5/1991 | Yamanashi et al. |
| 5,029,588 A | 7/1991 | Yock et al. |
| 5,178,150 A | 1/1993 | Silverstein et al. |
| 5,217,460 A | 6/1993 | Knoepfler |
| 5,238,004 A | 8/1993 | Sahatjian et al. |
| 5,240,003 A | 8/1993 | Lancee et al. |
| 5,254,088 A | 10/1993 | Lundquist et al. |
| 5,295,482 A | 3/1994 | Clare et al. |
| 5,318,589 A | 6/1994 | Lichtman |
| 5,324,284 A | 6/1994 | Imran |
| 5,331,966 A | 7/1994 | Bennett et al. |
| 5,334,193 A | 8/1994 | Nardella |
| 5,341,807 A | 8/1994 | Nardella |
| 5,377,685 A | 1/1995 | Kazi et al. |
| 5,383,874 A | 1/1995 | Jackson et al. |
| 5,385,146 A | 1/1995 | Goldreyer |
| 5,385,148 A | 1/1995 | Lesh et al. |
| 5,391,199 A | 2/1995 | Ben-Haim |
| 5,398,683 A | 3/1995 | Edwards et al. |
| 5,409,000 A * | 4/1995 | Imran ..................... A61B 8/12 600/374 |
| 5,423,811 A | 6/1995 | Imran et al. |
| 5,447,529 A | 9/1995 | Marchlinski et al. |
| 5,462,521 A | 10/1995 | Brucker et al. |
| 5,482,054 A | 1/1996 | Slater et al. |
| 5,485,849 A | 1/1996 | Panescu et al. |
| 5,494,042 A | 2/1996 | Panescu et al. |
| 5,500,012 A | 3/1996 | Brucker et al. |
| 5,520,683 A | 5/1996 | Subramaniam et al. |
| 5,571,088 A | 11/1996 | Lennox et al. |
| 5,573,535 A | 11/1996 | Viklund |
| 5,575,772 A | 11/1996 | Lennox |
| 5,579,764 A | 12/1996 | Goldreyer |
| 5,582,609 A | 12/1996 | Swanson et al. |
| 5,647,870 A | 7/1997 | Kordis et al. |
| 5,718,701 A | 2/1998 | Shai et al. |
| 5,722,402 A | 3/1998 | Swanson et al. |
| 5,762,067 A | 6/1998 | Dunham et al. |
| 5,788,636 A | 8/1998 | Curley |
| 5,792,064 A | 8/1998 | Panescu et al. |
| 5,800,482 A | 9/1998 | Pomeranz et al. |
| 5,820,568 A | 10/1998 | Willis |
| 5,830,213 A | 11/1998 | Panescu et al. |
| 5,833,621 A | 11/1998 | Panescu et al. |
| 5,836,990 A | 11/1998 | Li |
| 5,868,735 A | 2/1999 | Lafontaine |
| 5,871,483 A | 2/1999 | Jackson et al. |
| 5,871,526 A | 2/1999 | Gibbs et al. |
| 5,876,336 A | 3/1999 | Swanson et al. |
| 5,913,856 A | 6/1999 | Chia et al. |
| 5,916,213 A | 6/1999 | Haissaguerre et al. |
| 5,957,850 A | 9/1999 | Marian et al. |
| 6,004,269 A | 12/1999 | Crowley et al. |
| 6,027,500 A | 2/2000 | Buckles et al. |
| 6,050,994 A | 4/2000 | Sherman |
| 6,059,778 A | 5/2000 | Sherman |
| 6,064,905 A | 5/2000 | Webster, Jr. et al. |
| 6,070,094 A | 5/2000 | Swanson et al. |
| 6,083,170 A | 7/2000 | Ben-Haim |
| 6,083,222 A | 7/2000 | Klein et al. |
| 6,099,524 A | 8/2000 | Lipson et al. |
| 6,101,409 A | 8/2000 | Swanson et al. |
| 6,116,027 A | 9/2000 | Smith et al. |
| 6,120,476 A | 9/2000 | Fung et al. |
| 6,165,123 A | 12/2000 | Thompson |
| 6,171,305 B1 | 1/2001 | Sherman |
| 6,200,314 B1 | 3/2001 | Sherman |
| 6,206,831 B1 | 3/2001 | Suorsa et al. |
| 6,210,337 B1 | 4/2001 | Dunham et al. |
| 6,216,027 B1 | 4/2001 | Willis et al. |
| 6,224,557 B1 | 5/2001 | Ziel et al. |
| 6,233,491 B1 | 5/2001 | Kordis et al. |
| 6,241,754 B1 | 6/2001 | Swanson et al. |
| 6,270,493 B1 | 8/2001 | Lalonde et al. |
| 6,290,697 B1 | 9/2001 | Tu et al. |
| 6,352,534 B1 | 3/2002 | Paddock et al. |
| 6,395,325 B1 | 5/2002 | Hedge et al. |
| 6,400,981 B1 | 6/2002 | Govari |
| 6,423,002 B1 | 7/2002 | Hossack |
| 6,475,213 B1 | 11/2002 | Whayne et al. |
| 6,488,678 B2 | 12/2002 | Sherman |
| 6,491,710 B2 | 12/2002 | Satake |
| 6,508,767 B2 | 1/2003 | Burns et al. |
| 6,508,769 B2 | 1/2003 | Bonnefous |
| 6,508,803 B1 | 1/2003 | Horikawa et al. |
| 6,514,249 B1 * | 2/2003 | Maguire ................ A61B 18/00 606/37 |
| 6,516,667 B1 | 2/2003 | Broad et al. |
| 6,517,533 B1 | 2/2003 | Swaminathan |
| 6,517,534 B1 | 2/2003 | McGovern et al. |
| 6,537,271 B1 | 3/2003 | Murray et al. |
| 6,544,175 B1 | 4/2003 | Newman |
| 6,547,788 B1 | 4/2003 | Maguire et al. |
| 6,572,547 B2 | 6/2003 | Miller et al. |
| 6,575,966 B2 | 6/2003 | Lane et al. |
| 6,575,969 B1 | 6/2003 | Rittman et al. |
| 6,579,278 B1 | 6/2003 | Bencini |

(56) References Cited

U.S. PATENT DOCUMENTS

| | | |
|---|---|---|
| 6,582,372 B2 | 6/2003 | Poland |
| 6,589,182 B1 | 7/2003 | Loftman et al. |
| 6,592,525 B2 | 7/2003 | Miller et al. |
| 6,602,242 B1 | 8/2003 | Fung et al. |
| 6,620,103 B1 | 9/2003 | Bruce et al. |
| 6,632,179 B2 | 10/2003 | Wilson et al. |
| 6,638,222 B2 | 10/2003 | Chandrasekaran et al. |
| 6,640,120 B1 | 10/2003 | Swanson et al. |
| 6,647,281 B2 | 11/2003 | Morency |
| 6,656,174 B1 | 12/2003 | Hegde et al. |
| 6,658,279 B2 | 12/2003 | Swanson et al. |
| 6,666,862 B2 | 12/2003 | Jain et al. |
| 6,676,606 B2 | 1/2004 | Simpson et al. |
| 6,692,441 B1 | 2/2004 | Poland et al. |
| 6,705,992 B2 | 3/2004 | Gatzke |
| 6,709,396 B2 | 3/2004 | Flesch et al. |
| 6,711,429 B1 | 3/2004 | Gilboa et al. |
| 6,719,756 B1 | 4/2004 | Muntermann |
| 6,735,465 B2 | 5/2004 | Panescu |
| 6,736,814 B2 | 5/2004 | Manna et al. |
| 6,743,174 B2 | 6/2004 | Ng et al. |
| 6,773,402 B2 | 8/2004 | Govari et al. |
| 6,776,758 B2 | 8/2004 | Peszynski et al. |
| 6,796,979 B2 | 9/2004 | Lentz |
| 6,796,980 B2 | 9/2004 | Hall |
| 6,811,550 B2 | 11/2004 | Holland et al. |
| 6,824,517 B2 | 11/2004 | Salgo et al. |
| 6,837,884 B2 | 1/2005 | Woloszko |
| 6,845,264 B1 | 1/2005 | Skladnev et al. |
| 6,917,834 B2 | 7/2005 | Koblish et al. |
| 6,922,579 B2 | 7/2005 | Taimisto et al. |
| 6,923,808 B2 | 8/2005 | Taimisto |
| 6,932,811 B2 | 8/2005 | Hooven et al. |
| 6,945,938 B2 | 9/2005 | Grunwald |
| 6,950,689 B1 | 9/2005 | Willis et al. |
| 6,952,615 B2 | 10/2005 | Satake |
| 6,958,040 B2 | 10/2005 | Oliver et al. |
| 7,001,383 B2 | 2/2006 | Keidar |
| 7,037,264 B2 | 5/2006 | Poland |
| 7,047,068 B2 | 5/2006 | Haissaguerre |
| 7,097,643 B2 | 8/2006 | Cornelius et al. |
| 7,105,122 B2 | 9/2006 | Karason |
| 7,112,198 B2 | 9/2006 | Satake |
| 7,115,122 B1 | 10/2006 | Swanson et al. |
| 7,131,947 B2 | 11/2006 | Demers |
| 7,166,075 B2 | 1/2007 | Varghese et al. |
| 7,220,233 B2 | 5/2007 | Nita et al. |
| 7,232,433 B1 | 6/2007 | Schlesinger et al. |
| 7,247,155 B2 | 7/2007 | Hoey et al. |
| 7,270,634 B2 | 9/2007 | Scampini et al. |
| 7,288,088 B2 | 10/2007 | Swanson |
| 7,291,142 B2 | 11/2007 | Eberl et al. |
| 7,306,561 B2 | 12/2007 | Sathyanarayana |
| 7,335,052 B2 | 2/2008 | D'Sa |
| 7,347,820 B2 | 3/2008 | Bonnefous |
| 7,347,821 B2 | 3/2008 | Dkyba et al. |
| 7,347,857 B2 | 3/2008 | Anderson et al. |
| 7,361,144 B2 | 4/2008 | Levrier et al. |
| 7,422,591 B2 | 9/2008 | Phan |
| 7,438,714 B2 | 10/2008 | Phan |
| 7,455,669 B2 | 11/2008 | Swanson |
| 7,488,289 B2 | 2/2009 | Suorsa et al. |
| 7,507,205 B2 | 3/2009 | Borovsky et al. |
| 7,519,410 B2 | 4/2009 | Taimisto et al. |
| 7,529,393 B2 | 5/2009 | Peszynski et al. |
| 7,534,207 B2 | 5/2009 | Shehada et al. |
| 7,544,164 B2 | 6/2009 | Knowles et al. |
| 7,549,988 B2 | 6/2009 | Eberl et al. |
| 7,569,052 B2 | 8/2009 | Phan et al. |
| 7,578,791 B2 | 8/2009 | Rafter |
| 7,582,083 B2 | 9/2009 | Swanson |
| 7,585,310 B2 | 9/2009 | Phan et al. |
| 7,648,462 B2 | 1/2010 | Jenkins et al. |
| 7,697,972 B2 | 4/2010 | Verard et al. |
| 7,704,208 B2 | 4/2010 | Thiele |
| 7,720,420 B2 | 5/2010 | Kajita |
| 7,727,231 B2 | 6/2010 | Swanson |
| 7,736,362 B2 | 6/2010 | Eberl et al. |
| 7,740,629 B2 | 6/2010 | Anderson et al. |
| 7,758,508 B1 | 7/2010 | Thiele et al. |
| 7,766,833 B2 | 8/2010 | Lee et al. |
| 7,776,033 B2 | 8/2010 | Swanson |
| 7,785,324 B2 | 8/2010 | Eberl |
| 7,794,398 B2 | 9/2010 | Salgo |
| 7,796,789 B2 | 9/2010 | Salgo et al. |
| 7,799,025 B2 | 9/2010 | Wellman |
| 7,815,572 B2 | 10/2010 | Loupas |
| 7,819,863 B2 | 10/2010 | Eggers et al. |
| 7,837,624 B1 | 11/2010 | Hossack et al. |
| 7,859,170 B2 | 12/2010 | Knowles et al. |
| 7,862,561 B2 | 1/2011 | Swanson et al. |
| 7,862,562 B2 | 1/2011 | Eberl |
| 7,892,228 B2 | 2/2011 | Landis et al. |
| 7,918,850 B2 | 4/2011 | Govari et al. |
| 7,957,817 B1 | 6/2011 | Gillespie et al. |
| 8,016,822 B2 | 9/2011 | Swanson |
| 8,048,028 B2 | 11/2011 | Horn et al. |
| 8,128,617 B2 | 3/2012 | Bencini et al. |
| 8,414,579 B2 | 4/2013 | Kim et al. |
| 8,579,889 B2 | 11/2013 | Bencini |
| 8,657,814 B2 | 2/2014 | Werneth et al. |
| 8,740,900 B2 | 6/2014 | Kim et al. |
| 8,771,343 B2 | 7/2014 | Weber et al. |
| 8,894,643 B2 | 11/2014 | Watson et al. |
| 8,945,015 B2 | 2/2015 | Rankin et al. |
| 9,089,340 B2 | 7/2015 | Hastings et al. |
| 9,125,668 B2 | 9/2015 | Subramaniam et al. |
| 9,241,687 B2 | 1/2016 | McGee |
| 9,241,761 B2 * | 1/2016 | Rankin .............. A61B 18/1492 |
| 2001/0029371 A1 | 10/2001 | Kordis |
| 2002/0087208 A1 | 7/2002 | Koblish et al. |
| 2002/0198521 A1 | 12/2002 | Maguire |
| 2003/0013958 A1 | 1/2003 | Govari et al. |
| 2003/0088240 A1 | 5/2003 | Saadat |
| 2003/0158548 A1 | 8/2003 | Phan et al. |
| 2003/0158549 A1 | 8/2003 | Swanson |
| 2003/0229286 A1 | 12/2003 | Lenker |
| 2004/0006268 A1 | 1/2004 | Gilboa et al. |
| 2004/0082860 A1 | 4/2004 | Haissaguerre |
| 2004/0092806 A1 | 5/2004 | Sagon et al. |
| 2004/0116793 A1 | 6/2004 | Taimisto et al. |
| 2004/0147920 A1 | 7/2004 | Keidar |
| 2004/0162556 A1 | 8/2004 | Swanson |
| 2004/0186467 A1 | 9/2004 | Swanson et al. |
| 2004/0210136 A1 | 10/2004 | Varghese et al. |
| 2004/0215177 A1 | 10/2004 | Swanson |
| 2004/0215186 A1 | 10/2004 | Cornelius et al. |
| 2005/0033331 A1 | 2/2005 | Burnett et al. |
| 2005/0059862 A1 | 3/2005 | Phan |
| 2005/0059962 A1 | 3/2005 | Phan et al. |
| 2005/0059963 A1 | 3/2005 | Phan et al. |
| 2005/0059965 A1 | 3/2005 | Eberl et al. |
| 2005/0065506 A1 | 3/2005 | Phan |
| 2005/0065508 A1 | 3/2005 | Johnson et al. |
| 2005/0070894 A1 | 3/2005 | McClurken |
| 2005/0090817 A1 | 4/2005 | Phan |
| 2005/0119545 A1 | 6/2005 | Swanson |
| 2005/0119648 A1 | 6/2005 | Swanson |
| 2005/0119649 A1 | 6/2005 | Swanson |
| 2005/0119653 A1 | 6/2005 | Swanson |
| 2005/0119654 A1 | 6/2005 | Swanson et al. |
| 2005/0124881 A1 | 6/2005 | Kanai et al. |
| 2005/0187544 A1 | 8/2005 | Swanson et al. |
| 2005/0203597 A1 | 9/2005 | Yamazaki et al. |
| 2005/0228286 A1 | 10/2005 | Messerly et al. |
| 2005/0228504 A1 | 10/2005 | Demarais |
| 2005/0273060 A1 | 12/2005 | Levy et al. |
| 2006/0030919 A1 | 2/2006 | Mrva et al. |
| 2006/0089634 A1 | 4/2006 | Anderson et al. |
| 2006/0100522 A1 | 5/2006 | Yuan et al. |
| 2006/0161146 A1 | 7/2006 | Cornelius et al. |
| 2006/0247607 A1 | 11/2006 | Cornelius et al. |
| 2006/0247683 A1 | 11/2006 | Danek et al. |
| 2006/0253028 A1 | 11/2006 | Lam et al. |

(56) References Cited

U.S. PATENT DOCUMENTS

| | | |
|---|---|---|
| 2006/0253116 A1 | 11/2006 | Avitall et al. |
| 2007/0003811 A1 | 1/2007 | Zerfass et al. |
| 2007/0016054 A1 | 1/2007 | Yuan et al. |
| 2007/0016059 A1 | 1/2007 | Morimoto et al. |
| 2007/0016228 A1 | 1/2007 | Salas |
| 2007/0021744 A1 | 1/2007 | Creighton |
| 2007/0049925 A1 | 3/2007 | Phan et al. |
| 2007/0055225 A1 | 3/2007 | Dodd, III et al. |
| 2007/0073135 A1 | 3/2007 | Lee et al. |
| 2007/0088345 A1 | 4/2007 | Larson et al. |
| 2007/0165916 A1 | 7/2007 | Cloutier et al. |
| 2007/0167813 A1 | 7/2007 | Lee et al. |
| 2007/0238997 A1 | 10/2007 | Camus |
| 2007/0270794 A1 | 11/2007 | Anderson et al. |
| 2008/0009733 A1 | 1/2008 | Saksena |
| 2008/0015568 A1 | 1/2008 | Paul et al. |
| 2008/0025145 A1 | 1/2008 | Peszynski et al. |
| 2008/0058836 A1 | 3/2008 | Moll et al. |
| 2008/0086073 A1 | 4/2008 | McDaniel |
| 2008/0091109 A1 | 4/2008 | Abraham |
| 2008/0140065 A1 | 6/2008 | Rioux et al. |
| 2008/0161705 A1 | 7/2008 | Podmore et al. |
| 2008/0161795 A1 | 7/2008 | Wang et al. |
| 2008/0195089 A1 | 8/2008 | Thiagalingam et al. |
| 2008/0228111 A1 | 9/2008 | Nita |
| 2008/0243214 A1 | 10/2008 | Koblish |
| 2008/0275428 A1 | 11/2008 | Tegg et al. |
| 2008/0281322 A1 | 11/2008 | Sherman et al. |
| 2008/0287803 A1 | 11/2008 | Li et al. |
| 2008/0300454 A1 | 12/2008 | Goto |
| 2008/0312713 A1 | 12/2008 | Wilfley et al. |
| 2009/0005771 A1 | 1/2009 | Lieber et al. |
| 2009/0030312 A1 | 1/2009 | Hadjicostis |
| 2009/0048591 A1 | 2/2009 | Ibrahim et al. |
| 2009/0056344 A1 | 3/2009 | Poch |
| 2009/0062790 A1 | 3/2009 | Malchano et al. |
| 2009/0062795 A1 | 3/2009 | Vakharia et al. |
| 2009/0076390 A1 | 3/2009 | Lee et al. |
| 2009/0093810 A1 | 4/2009 | Subramaniam et al. |
| 2009/0093811 A1 | 4/2009 | Koblish et al. |
| 2009/0099472 A1 | 4/2009 | Remmert et al. |
| 2009/0131932 A1 | 5/2009 | Vakharia et al. |
| 2009/0163904 A1 | 6/2009 | Miller et al. |
| 2009/0171341 A1 | 7/2009 | Pope et al. |
| 2009/0182316 A1 | 7/2009 | Bencini |
| 2009/0216125 A1 | 8/2009 | Lenker |
| 2009/0240247 A1 | 9/2009 | Rioux et al. |
| 2009/0259274 A1 | 10/2009 | Simon et al. |
| 2009/0287202 A1 | 11/2009 | Ingle et al. |
| 2009/0292209 A1 | 11/2009 | Hadjicostis |
| 2009/0299355 A1 | 12/2009 | Bencini et al. |
| 2009/0299360 A1 | 12/2009 | Ormsby |
| 2010/0010487 A1 | 1/2010 | Phan et al. |
| 2010/0057072 A1 | 3/2010 | Roman et al. |
| 2010/0076402 A1 | 3/2010 | Mazzone et al. |
| 2010/0094274 A1 | 4/2010 | Narayan et al. |
| 2010/0106155 A1 | 4/2010 | Anderson et al. |
| 2010/0113938 A1 | 5/2010 | Park et al. |
| 2010/0145221 A1 | 6/2010 | Brunnett et al. |
| 2010/0152728 A1 | 6/2010 | Park et al. |
| 2010/0168557 A1 | 7/2010 | Deno et al. |
| 2010/0168568 A1 | 7/2010 | Sliwa |
| 2010/0168569 A1* | 7/2010 | Sliwa ............... A61B 8/0841 600/439 |
| 2010/0168570 A1 | 7/2010 | Sliwa et al. |
| 2010/0168831 A1 | 7/2010 | Korivi et al. |
| 2010/0249599 A1 | 9/2010 | Hastings et al. |
| 2010/0249603 A1 | 9/2010 | Hastings et al. |
| 2010/0249604 A1 | 9/2010 | Hastings et al. |
| 2010/0298826 A1 | 11/2010 | Leo et al. |
| 2010/0331658 A1 | 12/2010 | Kim et al. |
| 2011/0028820 A1 | 2/2011 | Lau et al. |
| 2011/0071400 A1 | 3/2011 | Hastings et al. |
| 2011/0071401 A1 | 3/2011 | Hastings et al. |
| 2011/0112569 A1 | 5/2011 | Friedman et al. |
| 2011/0125143 A1 | 5/2011 | Gross et al. |
| 2011/0130648 A1 | 6/2011 | Beeckler et al. |
| 2011/0144491 A1 | 6/2011 | Sliwa et al. |
| 2011/0144524 A1 | 6/2011 | Fish et al. |
| 2011/0160584 A1 | 6/2011 | Paul et al. |
| 2011/0201973 A1* | 8/2011 | Stephens ............... A61B 8/08 601/2 |
| 2011/0282249 A1 | 11/2011 | Tsoref et al. |
| 2011/0319782 A1 | 12/2011 | Sweeney et al. |
| 2012/0004547 A1 | 1/2012 | Harks et al. |
| 2012/0095347 A1 | 4/2012 | Adam et al. |
| 2012/0101398 A1 | 4/2012 | Ramanathan et al. |
| 2012/0116537 A1 | 5/2012 | Liebetanz |
| 2012/0136351 A1 | 5/2012 | Weekamp et al. |
| 2012/0172698 A1 | 7/2012 | Hastings et al. |
| 2012/0172727 A1 | 7/2012 | Hastings et al. |
| 2012/0172871 A1 | 7/2012 | Hastings et al. |
| 2012/0310064 A1 | 12/2012 | McGee |
| 2012/0330304 A1 | 12/2012 | Vegesna et al. |
| 2013/0023897 A1 | 1/2013 | Wallace |
| 2013/0066312 A1 | 3/2013 | Subramaniam et al. |
| 2013/0066315 A1 | 3/2013 | Subramaniam et al. |
| 2013/0079763 A1 | 3/2013 | Heckel et al. |
| 2013/0172715 A1 | 7/2013 | Just et al. |
| 2013/0172742 A1 | 7/2013 | Rankin et al. |
| 2013/0190747 A1 | 7/2013 | Koblish et al. |
| 2013/0197363 A1 | 8/2013 | Rankin et al. |
| 2013/0274582 A1 | 10/2013 | Afonso et al. |
| 2013/0331739 A1 | 12/2013 | Gertner |
| 2014/0012251 A1 | 1/2014 | Himmelstein et al. |
| 2014/0066764 A1 | 3/2014 | Subramaniam et al. |
| 2014/0075753 A1 | 3/2014 | Haarer et al. |
| 2014/0081113 A1 | 3/2014 | Cohen et al. |
| 2014/0081262 A1 | 3/2014 | Koblish et al. |
| 2014/0107636 A1 | 4/2014 | Bencini |
| 2014/0276052 A1 | 9/2014 | Rankin et al. |
| 2015/0133914 A1 | 5/2015 | Koblish |
| 2015/0133920 A1 | 5/2015 | Rankin et al. |
| 2015/0374436 A1 | 12/2015 | Subramaniam et al. |
| 2016/0100884 A1 | 4/2016 | Fay et al. |

FOREIGN PATENT DOCUMENTS

| | | |
|---|---|---|
| CA | 2847846 A1 | 3/2013 |
| CN | 1269708 A | 10/2000 |
| CN | 1455655 A | 11/2003 |
| CN | 1942145 A | 4/2007 |
| CN | 102573986 A | 7/2012 |
| CN | 103917185 A | 7/2014 |
| CN | 103987336 A | 8/2014 |
| CN | 104619259 A | 5/2015 |
| CN | 104661609 A | 5/2015 |
| EP | 1343426 B1 | 9/2003 |
| EP | 1343427 B1 | 9/2003 |
| EP | 1502542 A1 | 2/2005 |
| EP | 1547537 A1 | 6/2005 |
| EP | 0985423 B1 | 4/2006 |
| EP | 1717601 A2 | 11/2006 |
| EP | 1935332 A2 | 6/2008 |
| EP | 2755587 A | 7/2014 |
| EP | 2755588 A | 7/2014 |
| EP | 2136702 B1 | 7/2015 |
| JP | 2000000242 A | 1/2000 |
| JP | 200083918 A | 3/2000 |
| JP | 2000504242 A | 4/2000 |
| JP | 2002528039 A | 8/2002 |
| JP | 2003504090 A | 2/2003 |
| JP | 2004503335 A | 2/2004 |
| JP | 2006239414 A | 9/2006 |
| JP | 2007163559 A | 6/2007 |
| JP | 2007244857 A | 9/2007 |
| JP | 2009142653 A | 12/2008 |
| JP | 2009518150 A | 5/2009 |
| JP | 2010522623 A | 7/2010 |
| JP | 2011525842 A | 9/2011 |
| JP | 2012531967 A | 12/2012 |
| JP | 5336465 B2 | 11/2013 |
| JP | 2014012174 A | 1/2014 |
| JP | 2014531244 A | 11/2014 |

(56) References Cited

FOREIGN PATENT DOCUMENTS

| | | |
|---|---|---|
| JP | 2015501162 A | 1/2015 |
| JP | 2015509027 A | 3/2015 |
| KR | 20100021401 A | 2/2010 |
| KR | 101490374 B1 | 2/2015 |
| WO | WO199221278 A1 | 12/1992 |
| WO | WO9413358 A1 | 6/1994 |
| WO | WO199725916 A1 | 7/1997 |
| WO | WO199725917 A1 | 7/1997 |
| WO | WO199736541 A1 | 10/1997 |
| WO | 1997045156 A2 | 12/1997 |
| WO | WO199858681 A2 | 12/1998 |
| WO | 1999009879 A1 | 3/1999 |
| WO | WO1999027862 A1 | 6/1999 |
| WO | WO2000029062 A2 | 5/2000 |
| WO | WO2007079278 A1 | 7/2001 |
| WO | WO200158372 A1 | 8/2001 |
| WO | WO2001064145 A1 | 9/2001 |
| WO | WO2001068173 A2 | 9/2001 |
| WO | WO0205868 A2 | 1/2002 |
| WO | WO2002005868 A2 | 1/2002 |
| WO | WO2002009599 A2 | 2/2002 |
| WO | WO2002019934 A1 | 3/2002 |
| WO | WO200247569 A1 | 6/2002 |
| WO | WO2002102234 A2 | 12/2002 |
| WO | WO2003039338 A2 | 5/2003 |
| WO | WO2008046031 A2 | 4/2008 |
| WO | WO2008118992 A1 | 10/2008 |
| WO | WO2009032421 A2 | 3/2009 |
| WO | 2009048824 A1 | 4/2009 |
| WO | 2010054409 A1 | 5/2010 |
| WO | WO2010056771 A1 | 5/2010 |
| WO | 2010082146 A1 | 7/2010 |
| WO | 2011008444 A1 | 1/2011 |
| WO | 2011033421 A1 | 3/2011 |
| WO | WO2011024133 A1 | 3/2011 |
| WO | WO2011089537 A1 | 7/2011 |
| WO | 2011101778 A1 | 8/2011 |
| WO | WO2011095937 A1 | 8/2011 |
| WO | 2012001595 A1 | 1/2012 |
| WO | WO2010001595 A1 | 1/2012 |
| WO | WO2012001595 A1 | 1/2012 |
| WO | WO2012049621 A1 | 4/2012 |
| WO | WO2012066430 A1 | 5/2012 |
| WO | 2012161880 A1 | 11/2012 |
| WO | 2012166239 A1 | 12/2012 |
| WO | 2013040201 A2 | 3/2013 |
| WO | 2013040297 A1 | 3/2013 |
| WO | 2014152575 A2 | 9/2014 |

OTHER PUBLICATIONS

International Preliminary Examination Report issued in PCT/US2013/060612, dated Mar. 24, 2015, 10 pages.
International Preliminary Report on Patentability issued in PCT/US2013/058105, dated Mar. 10, 2015.
International Search Report and Written Opinion issued in PCT/US2008/058324, dated Aug. 18, 2008, 11 pages.
International Search Report and Written Opinion issued in PCT/US2012/031819, dated Sep. 27, 2012, 16 pages.
International Search Report and Written Opinion issued in PCT/US2012/055309, dated Nov. 19, 2012, 13 pages.
International Search Report and Written Opinion issued in PCT/US2012/072061, dated Mar. 21, 2013, 9 pages.
International Search Report and Written Opinion issued in PCT/US2013/020503, dated Mar. 20, 2013, 10 pages.
International Search Report and Written Opinion issued in PCT/US2013/058105, dated Nov. 22, 2013, 16 pages.
International Search Report and Written Opinion issued in PCT/US2013/060612, dated Feb. 28, 2014, 16 pages.
International Search Report and Written Opinion issued in PCT/US2014/027491, dated Sep. 23, 2014, 17 pages.
Invitation to Pay Additional Fees and Partial International Search Report issued in PCT/US2014/027491, dated Jul. 28, 2014, 5 pages.
Machi MD, Junji, "Prevention of Dispersive Pad Skin Burns During RFA by a Simple Method", Editorial Comment, Surg Laparosc Endosc Percutan Tech, vol. 13, No. 6, Dec. 2003, pp. 372-373.
Neufeld, Gordon R. et al., "Electrical Impedance Properties of the Body and the Problem of Alternate-site Burns During Electrosurgery", Medical Instrumentation, vol. 19, No. 2, Mar.-Apr. 1985, pp. 83-87.
Partial International Search Report issued in PCT/US2012/055155, dated Dec. 20, 2012, 7 pages.
Steinke, Karin et al., "Dispersive Pad Site burns With Modern Radiofrequency Ablation Equipment", Surg Laparosc Endosc Percutan Tech, vol. 13, No. 6, Dec. 2003, pp. 366-371.
Extended European Search Report issued in EP Application No. 15174537.9, dated Mar. 2, 2016, 7 pages.
Haverkamp, W., et. al. Coagulation of Ventricular Myocardium Using Radiofrequency Alternating Current: Bio-Physical Aspects arid Experimental Findings. PACE, 12:187-195, Jan. 1989, Part II.
International Preliminary Report on Patentability issued in PCT/US2008/058324, dated Sep. 29, 2009, 9 pages.
International Preliminary Report on Patentability issued in PCT/US2012/055155, dated Mar. 18, 2014, 11 pages.
International Preliminary Report on Patentability issued in PCT/US2012/055309, dated Mar. 18, 2014, 8 pages.
International Preliminary Report on Patentability issued in PCT/US2013/056211, dated Feb. 24, 2015, 5 pages.
International Preliminary Report on Patentability issued in PCT/US2013/060194, dated Mar. 24, 2015, 6 pages.
International Preliminary Report on Patentablity issued in PCT/US2013/060183, dated Mar. 24, 2015, 6 pages.
International Search Report and Written Opinion issued in PCT/US2012/055155, dated Mar. 11, 2013, 19 pages.
International Search Report and Written Opinion issued in PCT/US2013/021013, dated Apr. 5, 2013, 14 pages.
International Search Report and Written Opinion issued in PCT/US2013/056211, dated Jan. 20, 2014.
International Search Report and Written Opinion issued in PCT/US2013/060183, dated Jan. 27, 2014, 10 pages.
International Search Report and Written Opinion issued in PCT/US2013/060194, dated Jan. 29, 2014.
International Search Report and Written Opinion issued in PCT/US2013/060194, dated Jan. 29, 2014, 10 pages.
International Search Report and Written Opinion issued in PCT/US2015/021300, dated Jun. 9, 2015, 11 pages.
International Search Report and Written Opinion issued in PCT/US2015/055173, dated Jan. 18, 2016, 11 pages.
International Search Report and Written Opinion issued in PCT/US2015/057242, dated Jan. 15, 2016, 11 pages.
International Search Report and Written Opinion issued in PCT/US2015/031591, dated Aug. 17, 2015, 11 pages.
Patriciu, A. et al., "Detecting Skin Burns induced by Surface Electrodes", published in Engineering in Medicine and Biology Society, 2001. Proceedings of the 23rd Annual international Conference of the IEEE, vol. 3, pp. 3129-3131.
Piorkowski, Christopher et al., "First in Human Validation of Impedance-Based Catheter Tip-to-Tissue Contact Assessment in the Left Atrium", Journal of Cardiovascular Electrophysiology, vol. 20, No. 12, Dec. 1, 2009, pp. 1366-1373.
Pires, L. A., et. al. Temperature-guided Radiofrequency Catheter Ablation of Closed-Chest Ventricular Myocardium with a Novel Thermistor-Tipped Catheter. American Heart Journal, 127(6):1614-1618, Jun. 1994.
Price, Adam et al., "Novel Ablation Catheter Technology that Improves Mapping Resolution and Monitoring of Lesion Maturation", The Journal of Innovations in Cardiac Rhythm Management, vol. 3, 2002, pp. 599-609.
Price, Adam et al., "PO3-39 Pin Electrodes Improve Resolution: Enhanced Monitoring of Radiofrequency Lesions in the Voltage and Frequency Domains", Heart Rhythm 2010, 31st Annual Scientific Sessions, May 12-15 in Denver Colorado.
Ring, E. R., et. al. Catheter Ablation of the Ventricular Septum with Radiofrequency Energy. American Heart Journal, 117(6):1233-1240, Jun. 1989.

(56) References Cited

OTHER PUBLICATIONS

Zachary, J.M. et al., "PO4-86 Pin Electrodes Provide Enhanced Resolution Enabling Titration of Radiofrequency Duration to Lesion Maturation", Heart Rhythm 2011, 32 Annual Scientific Sessions, May 4-7, San Francisco, CA.

* cited by examiner

ABLATION PROBE WITH FLUID-BASED ACOUSTIC COUPLING FOR ULTRASONIC TISSUE IMAGING

CROSS-REFERENCE TO RELATED APPLICATION

This application is a division of U.S. application Ser. No. 13/735,358, filed Jan. 7, 2013, which claims priority to Provisional Application No. 61/592,908, filed Jan. 31, 2012, which is herein incorporated by reference in its entirety.

TECHNICAL FIELD

The present disclosure relates generally to devices and systems for imaging tissue within the body during an ablation procedure. More specifically, the present disclosure relates to an ablation probe with ultrasonic imaging capabilities.

BACKGROUND

In ablation therapy, it is often necessary to determine various characteristics of body tissue at a target ablation site within the body. In interventional cardiac electrophysiology (EP) procedures, for example, it is often necessary for the physician to determine the condition of cardiac tissue at a target ablation site in or near the heart. During some EP procedures, the physician may deliver a mapping catheter through a main vein or artery into an interior region of the heart to be treated. Using the mapping catheter, the physician may then determine the source of a cardiac rhythm disturbance or abnormality by placing a number of mapping elements carried by the catheter into contact with the adjacent cardiac tissue and then operate the catheter to generate an electrophysiology map of the interior region of the heart. Once a map of the heart is generated, the physician may then advance an ablation catheter into the heart, and position an ablation electrode carried by the catheter tip near the targeted cardiac tissue to ablate the tissue and form a lesion, thereby treating the cardiac rhythm disturbance or abnormality. In some techniques, the ablation catheter itself may include a number of mapping electrodes, allowing the same device to be used for both mapping and ablation.

Various ultrasound-based imaging catheters and probes have been developed for directly visualizing body tissue in applications such as interventional cardiology, interventional radiology, and electrophysiology. For interventional cardiac electrophysiology procedures, for example, ultrasound imaging devices have been developed that permit the visualization of anatomical structures of the heart directly and in real-time. In some electrophysiology procedures, for example, ultrasound catheters may be used to image the intra-atrial septum, to guide transseptal crossing of the atrial septum, to locate and image the pulmonary veins, and to monitor the atrial chambers of the heart for signs of a perforation and pericardial effusion.

Many ultrasound-based imaging systems comprise an imaging probe that is separate from the mapping and ablation catheters used to perform therapy on the patient. As a result, a position tracking system is sometimes used to track the location of each device within the body. In some procedures, it may be difficult for the physician to quickly and accurately determine the condition of tissue to be ablated. Moreover, the images obtained using many ultrasound-based imaging systems are often difficult to read and understand without reference to images obtained from a separate imaging system such as a fluoroscopic imaging system.

SUMMARY

The present disclosure relates generally to devices and systems for imaging tissue within the body during an ablation procedure.

In Example 1, an ablation probe for treating and imaging body tissue comprises: an elongate probe body having a proximal section and a distal section; an ablation electrode tip coupled to the distal section of the elongate probe body, the ablation electrode tip configured for delivering ablation energy to body tissue; a plurality of acoustic openings disposed through the ablation electrode tip; a plurality of ultrasonic imaging sensors disposed within an interior lumen of the ablation electrode tip; an acoustically transparent member disposed between the ultrasonic imaging sensors and the acoustic openings; and a fluid channel interposed between the ultrasonic imaging sensors and the acoustically transparent member.

In Example 2, the probe according to Example 1, wherein each ultrasonic imaging sensor is configured to transmit ultrasonic waves through the fluid channel, the acoustically transparent member, and a corresponding one of the acoustic openings.

In Example 3, the probe according to any of Examples 1 or 2, wherein the ablation electrode tip comprises a tubular-shaped metal shell.

In Example 4, the probe according to any of Examples 1-3, wherein the acoustic openings are located circumferentially about the ablation electrode tip.

In Example 5, the probe according to any of Examples 1-4, wherein the ablation electrode tip further includes a plurality of irrigation ports.

In Example 6, the probe according to Example 5, wherein the irrigation ports are located circumferentially about the ablation electrode tip.

In Example 7, the probe according to any of Examples 5-6, wherein the irrigation ports are located distally and/or proximally of the acoustic openings.

In Example 8, the probe according to any of Examples 5-7, wherein the ultrasonic imaging sensors are located within the interior lumen of the ablation electrode tip at a location proximal to the irrigation ports.

In Example 9, the probe according to any of Examples 1-8, wherein the ultrasonic imaging sensors are each configured for transmitting laterally-directed ultrasonic waves from a side of the ablation electrode tip.

In Example 10, the probe of according to any of Examples 1-9, further comprising at least one additional ultrasonic imaging sensor disposed within the ablation electrode tip, the at least one additional ultrasonic imaging sensor configured for transmitting ultrasonic waves in a distal direction away from a distal end of the ablation electrode tip.

In Example 11, the probe according to Example 10, wherein the acoustically transparent member is further disposed between the at least one additional ultrasonic imaging sensor and a distal-facing acoustic opening disposed through the ablation electrode tip, and wherein the fluid channel is further interposed between the at least one additional ultrasonic imaging sensor and the distal-facing acoustic opening.

In Example 12, the probe according to any of Examples 1-10, wherein the acoustically transparent member comprises a tubular-shaped shell.

In Example 13, the probe according to any of Examples 1-12, wherein fluid within the fluid channel acoustically couples the ultrasonic imaging sensors to the body tissue.

In Example 14, the probe according to any of Examples 1-13, further comprising an insert configured for supporting the ultrasonic imaging sensors within the interior lumen of the ablation electrode tip.

In Example 15, the probe according to Example 14, wherein the insert comprises a cylindrically-shaped insert body including a plurality of recesses each configured for receiving an ultrasonic transducer therein.

In Example 16, the probe according to any of Examples 14-15, wherein a transmitting face of each ultrasonic imaging sensor is substantially flush with an outer surface of the insert body.

In Example 17, the probe according to any of Examples 14-16, wherein the interior lumen of the ablation electrode tip includes a proximal fluid chamber and a distal fluid chamber, wherein the proximal and distal fluid chambers are separated by the insert.

In Example 18, an ablation probe for treating and imaging body tissue comprises: an elongate probe body having a proximal section and a distal section; an ablation electrode tip coupled to the distal section of the elongate probe body, the ablation electrode tip configured for delivering ablation energy to body tissue; a plurality of acoustic openings disposed through a side of the ablation electrode tip; an insert disposed within an interior lumen of the ablation electrode tip; a plurality of lateral-facing ultrasonic imaging sensors coupled to the insert, the lateral-facing ultrasonic imaging sensors configured for transmitting ultrasonic waves from a side of the ablation electrode tip; an acoustically transparent member disposed between the lateral-facing ultrasonic imaging sensors and the acoustic openings; a fluid channel interposed between the lateral-facing ultrasonic imaging sensors and the acoustically transparent member; and at least one distal-facing ultrasonic imaging sensor disposed within the interior lumen of the ablation electrode, the distal-facing ultrasonic imaging sensor configured for transmitting ultrasonic waves in a distal direction away from a distal end of the ablation electrode tip.

In Example 19, an ablation and ultrasound imaging system comprises: an ablation probe including an ablation electrode tip configured for delivering ablation energy to body tissue, the ablation electrode tip comprising a plurality of acoustic openings disposed through the ablation electrode tip, a plurality of ultrasonic imaging sensors disposed within an interior lumen of the ablation electrode tip, an acoustically transparent member disposed between the ultrasonic imaging sensors and the acoustic openings, and a fluid channel interposed between the ultrasonic imaging sensors and the acoustically transparent member. The system further comprises a fluid source configured for delivering cooling fluid to the ablation electrode tip, the cooling fluid acoustically coupling the ultrasonic imaging sensors to the body tissue; an ablation therapy module configured for generating and supplying an electrical signal to the ablation electrode tip; and an ultrasound imaging module configured for processing ultrasonic imaging signals received from the ultrasonic imaging sensors.

In Example 20, the system according to Example 19, wherein the ultrasonic imaging module comprises a signal generator configured to generate control signals for controlling each ultrasonic imaging sensor; and an image processor configured for processing electrical signals received from each ultrasonic imaging sensor and generating a plurality of ultrasonic images.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
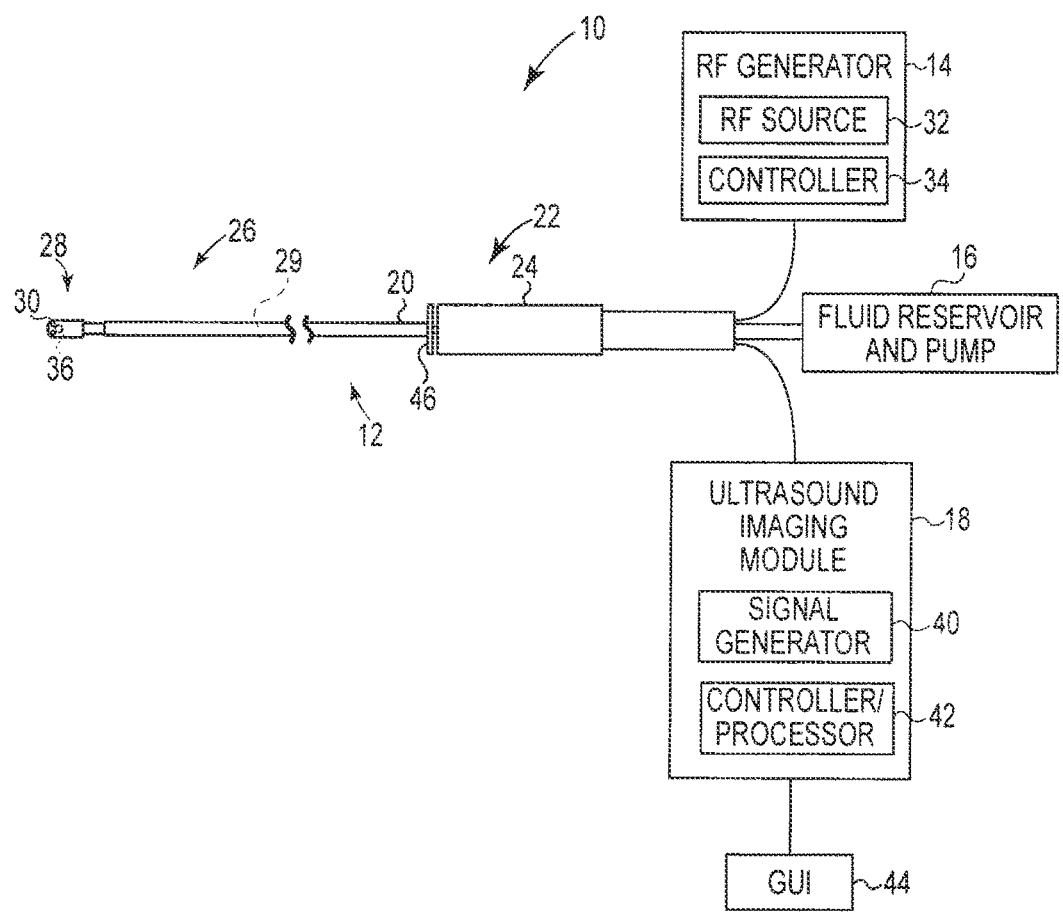
FIG. 1 is a schematic view of a combined ablation and imaging system in accordance with an illustrative embodiment.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of a combined ablation and imaging system 10 in accordance with an illustrative embodiment. As shown in FIG. 1, the system 10 includes a combined ablation and ultrasonic imaging probe 12, an RF generator 14, a fluid reservoir and pump 16, and an ultrasonic imaging module 18. The probe 12 comprises an elongate probe body 20 having a proximal section 22 equipped with a handle assembly 24, and a deflectable distal section 26 including an ablation electrode tip 28. The probe body 20 includes an internal cooling fluid lumen 29 fluidly coupled to the fluid reservoir and pump 16, which supplies cooling fluid, such as saline, through the probe body 20 to a number of irrigation ports 30 in the ablation electrode tip 28. The probe body 20 may further include additional lumens or other tubular elements for supporting electrical conductors, additional fluid lumens, a thermocouple, an insertable stylet, as well as other components. In some embodiments, the probe body 20 comprises flexible plastic tubing with a braided metal mesh to increase the rotational stiffness of the body 20.

The RF generator 14 is configured for generating RF energy for performing ablation procedures using the ablation electrode tip 28. The RF generator 14 includes an RF energy source 32 and a controller 34 for controlling the timing and level of the RF energy delivered by the tip 28. During an ablation procedure, the RF generator 14 is configured to deliver ablation energy to the tip 28 in a controlled manner to ablate any sites identified or targeted for ablation. Other types of ablation sources in addition to or in lieu of the RF generator 14 can also be used for ablating target sites. Examples of other types of ablation sources can include, but are not limited to, microwave generators, acoustic generators, cryoablation generators, and laser/optical generators.

The ultrasonic imaging module 18 is configured for generating high resolution ultrasonic images (e.g., A, M, or B-mode images) of anatomical structures within the body based on signals received from several ultrasonic imaging sensors 36 located within the probe tip 28. In the embodiment of FIG. 1, the ultrasonic imaging module 18 includes an ultrasonic signal generator 40 and an image processor 42. The ultrasonic signal generator 40 is configured to provide electrical signals for controlling each of the ultrasonic imaging sensors 36. The imaging signals received back from the ultrasonic imaging sensors 36, in turn, are fed to the image processor 42, which processes the signals and generates images that can be displayed on a graphical user interface (GUI) 44. In certain embodiments, for example, the ultrasonic images displayed on the GUI 44 can be used to assist the physician with advancing the probe 12 through the body and to perform an ablation procedure. In cardiac ablation procedures, for example, the ultrasonic images generated from the ultrasound signals can be used to confirm tissue contact of the probe 12 within the heart or surrounding anatomy, to determine the orientation of the probe 12 within the body, to determine the tissue depth of the tissue at a target ablation site, and/or to visualize the progression of a lesion being formed in the tissue.

Various characteristics associated with the ultrasonic imaging sensors 36 as well as the circuitry within the ultrasonic imaging module 18 can be controlled to permit the sensors 36 to accurately detect tissue boundaries (e.g., blood or other bodily fluids), lesion formation and progression, as well as other characteristics of the tissue before, during, and/or after the ablation procedure. Example tissue characteristics that can be visualized using the probe 12 include, but are not limited to, the presence of fluid vaporization inside the tissue, the existence of a prior scar, the size and shape of a lesion being formed, as well as structures adjacent to heart tissue (e.g., lungs, esophagus). The depth at which the ultrasonic imaging sensors 36 can visualize anatomical structures within the body is dependent on the mechanical characteristics of the sensors 36, the electrical characteristics of the sensor circuitry including the drive frequency of the signal generator 40, the boundary conditions and degree of attenuation between the sensors 36 and the surrounding anatomy, as well as other factors.

In some embodiments, the probe 12 further includes a steering mechanism to permit the operator to deflect and steer the probe 12 within the body. In one embodiment, for example, a steering member such as a steering knob 46 rotatably coupled to the handle 24 can be used to deflect the ablation electrode tip 28 in one or multiple directions relative to a longitudinal axis of the probe body 20. Rotational movement of the steering knob 46 in a first direction relative to the handle 24 causes a steering wire within the probe body 20 to move proximally relative to the probe body 20, which, in turn, bends the distal section 26 of the probe body 20 into a particular shape such as an arced shape. Rotational movement of the steering knob 46 in the opposite direction, in turn, causes the distal section 26 of the probe body 20 to return to its original shape, as shown. To assist in the deflection, and in some embodiments, the probe body 20 includes one or more regions made of a lower durometer material than the other portions of the probe body 20.

Although the system 10 is described in the context of a medical system for use in intracardiac electrophysiology procedures for diagnosing and treating the heart, in other embodiments the system 10 may be used for treating, diagnosing, or otherwise visualizing other anatomical structures such as the prostate, brain, gall bladder, uterus, esophagus, and/or other regions in the body. Moreover, many of the elements in FIG. 1 are functional in nature, and are not meant to limit the structure that performs these functions in any manner. For example, several of the functional blocks can be embodied in a single device or one or more of the functional blocks can be embodied in multiple devices.

Figure 2:
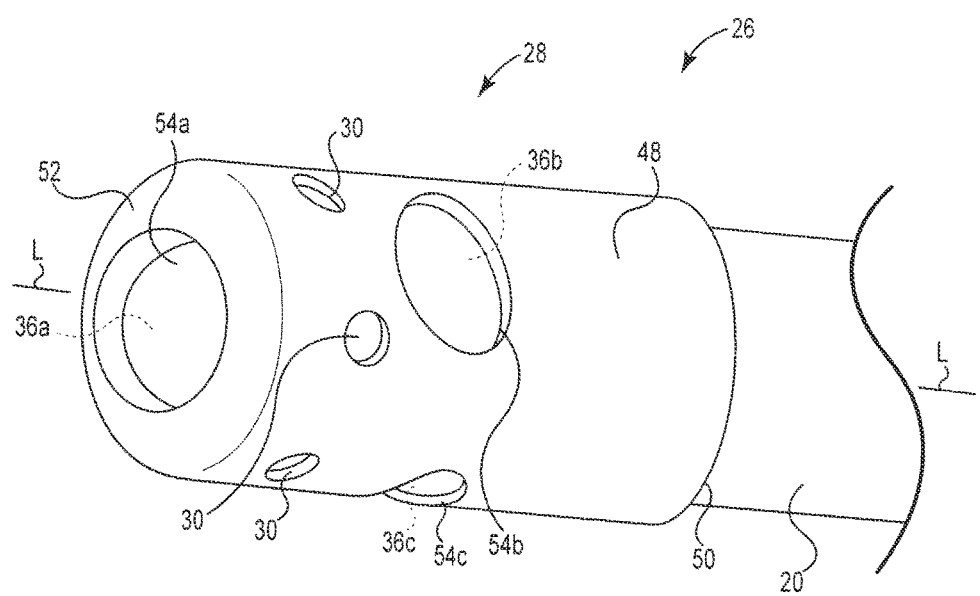
FIG. 2 is a perspective view showing the distal section of the combined ablation and ultrasonic imaging probe of FIG. 1 in greater detail.

FIG. 2 is a perspective view showing the distal section 26 of the probe 12 of FIG. 1 in greater detail. As can be further seen in FIG. 2, the ablation electrode tip 28 includes an RF ablation electrode 48 configured for delivering ablation energy to body tissue surrounding the tip 28. In the embodiment of FIG. 2, the RF ablation electrode 48 comprises a tubular-shaped metal shell that extends from a distal end 50 of the probe body 20 to a distal end 52 of the tip 28. A number of exposed openings 54a, 54b, 54c, 54d disposed through the ablation electrode tip 28 form acoustic openings that permit ultrasonic waves transmitted by the ultrasonic imaging sensors 36a, 36b, 36c, 36d to pass through the tip 28 and into the surrounding tissue. The reflected ultrasonic waves received back from the tissue pass through the acoustic openings 54a, 54b, 54c, 54d and are sensed by the ultrasonic imaging sensors 36a, 36b, 36c, 36d operating in a receive mode. In some embodiments, the acoustic openings 54a, 54b, 54c, 54d comprise exposed openings or apertures formed through the wall of the ablation electrode tip 28.

In addition to serving as an ablation electrode, the RF ablation electrode 48 also functions as a housing that contains the ultrasonic imaging sensors 36a, 36b, 36c, 36d, the electrical conductors coupling the RF ablation electrode 48 to the RF generator 14, the electrical conductors coupling the ultrasonic imaging sensors 36a, 36b, 36c, 36d to the ultrasonic imaging module 18, one or more steering wires of the steering mechanism, as well as other components. In certain embodiments, the RF ablation electrode 48 comprises an electrically conductive alloy such as platinum-iridium, which in addition to serving as an electrode for providing ablation therapy, is also used as a fluoroscopic marker to determine the location of the ablation electrode tip 28 within the body using fluoroscopy.

In the embodiment of FIG. 2, the probe 12 includes a distal-facing ultrasonic imaging sensor 36a located at or near the distal end 52 of the ablation electrode tip 28. The ultrasonic sensor 36a is configured to transmit ultrasonic waves primarily in a forward or distal direction away from the distal end 52 of the ablation electrode tip 28. A second set of ultrasonic imaging sensors 36b, 36c, 36d disposed within the tip 28 at a location proximal to the distal-facing ultrasonic imaging sensor 36a are configured to transmit ultrasonic waves primarily in a lateral or side-facing direction away from the side of the ablation electrode tip 28. The reflected waves received back from the ultrasonic imaging sensors 36a, 36b, 36c, 36d produces signals that can be used by the ultrasonic imaging module 18 to generate images of the surrounding body tissue.

In some embodiments, the ultrasonic imaging sensors 36a, 36b, 36c, 36d each comprise piezoelectric transducers formed of a piezoceramic material such as lead zirconate titanate (PZT) or a piezoelectric polymer such as polyvinylidene fluoride (PVDF). In some embodiments, the ablation electrode tip 28 includes three laterally-facing ultrasonic imaging sensors 36b, 36c, 36d each oriented circumferentially at 120° intervals apart from each other about the tip 28 for use in imaging tissue located adjacent to the sides of the tip 28. In other embodiments, a greater or lesser number of laterally-facing ultrasonic imaging sensors are employed for imaging tissue adjacent to the sides of the probe tip 28.

In the embodiment of FIG. 2, the ablation electrode tip 28 has an open irrigated configuration including a number of irrigation ports 30 used to deliver cooling fluid to cool the tip 28 and the surrounding tissue. In other embodiments, the ablation electrode tip 28 has a closed irrigation configuration in which the cooling fluid is recirculated through the tip 28 without being ejected into the surrounding tissue. In some embodiments, the ablation electrode tip 28 comprises six irrigation ports 30 each disposed circumferentially at 60° intervals apart from each other about the tip 28 and at a location proximal to the distal-facing ultrasonic sensor 36a and distal to the location of the laterally-facing ultrasonic sensors 36b, 36c, 36d. In other embodiments, a greater or lesser number of fluid irrigation ports 30 are employed. In some embodiments, the fluid irrigation ports 30 are circular in shape, and have a diameter in the range of approximately 0.01 inches to 0.02 inches. The size, number, and/or positioning of the irrigation ports 30 can vary, however.

During ablation therapy, cooling fluid is used to control the temperature and reduce coagulum formation on the ablation electrode tip 28, thus preventing an impedance rise of the tissue in contact with the tip 28 and increasing the transfer of RF ablation energy delivered into the tissue. In certain embodiments, and as discussed further herein, the cooling fluid also serves as an impedance matching layer to acoustically couple the ultrasonic sensors 36a, 36b, 36c, 36d to the surrounding body tissue, thus decreasing reflections that can occur at the interface between the tissue and the sensors 36a, 36b, 36c, 36d.

Figure 3:
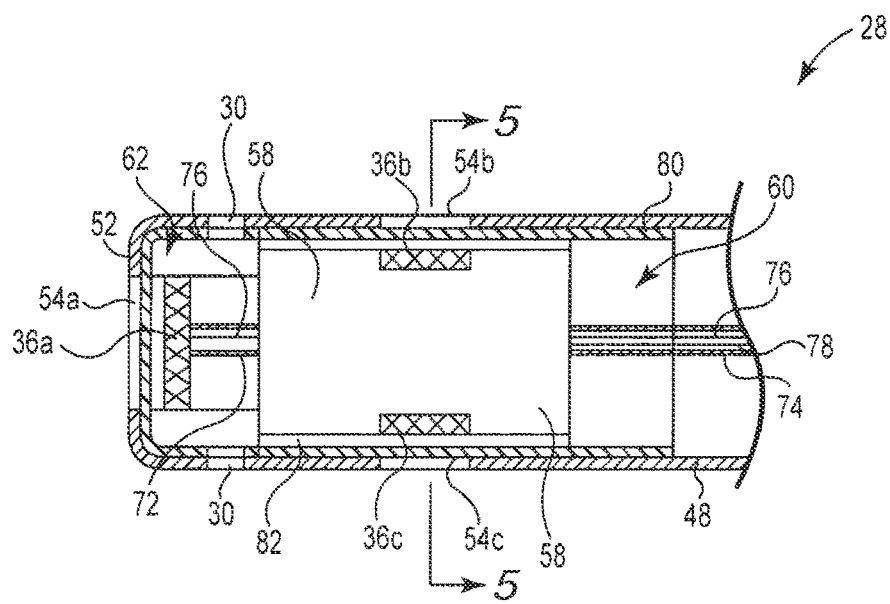
FIG. 3 is a schematic view showing an interior portion of the ablation electrode tip in accordance with an illustrative embodiment.
Figure 4:
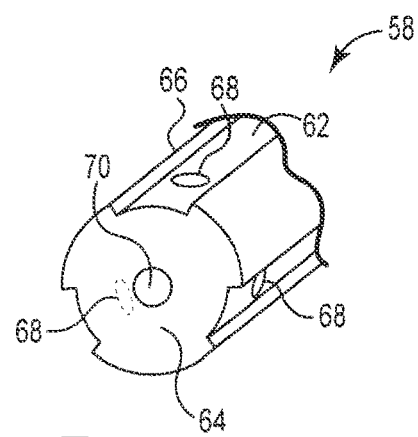
FIG. 4 is a perspective view of the tip insert of FIG. 3.

FIG. 3 is a schematic view showing an interior portion of the ablation electrode tip 28 in accordance with an illustrative embodiment. As shown in FIG. 3, the ablation electrode tip 28 includes a distal tip insert 58 configured to divide the interior of the probe tip 28 into a proximal fluid chamber 60 and a distal fluid chamber 62. As can be further seen in conjunction with FIG. 4, the distal insert 58 comprises a cylindrically-shaped body 64 having an outer extent 66 with a number of recesses 68 each configured to receive a corresponding one of the lateral-facing ultrasonic imaging sensors 36b, 36c, 36c therein. In certain embodiments, for example, the distal insert 58 comprises a stainless steel body having recesses 68 sized and shaped to frictionally receive the ultrasonic imaging sensors 36b, 36c, 36d by press-fitting the sensors 36b, 36c, 36d into the recesses 68. In some embodiments, the depth of the recesses 68 are configured such that the transmitting face of the ultrasonic sensors 36b, 36c, 36d lie substantially flush with the outer extent 66 of the insert body 64. In use, the insert body 64 separates the proximal fluid chamber 60 from the distal fluid chamber 62, creating a back pressure as fluid enters the proximal fluid chamber 60. This back pressure causes the fluid to circulate before being forced into the distal fluid chamber 62.

An internal bore 70 extending through the insert body 64 is configured to receive electrical conductors used for electrically coupling the ultrasonic sensors 36a, 36b, 36c, 36d to the ultrasonic imaging module 18. As can be further seen in FIG. 3, for example, the interior lumen 70 of the insert body 64 is connected at both ends to tubular members 72, 74 that contain electrical conductors 76, 78 for the ultrasonic sensors 36a, 36b, 36c, 36d.

Figure 5:
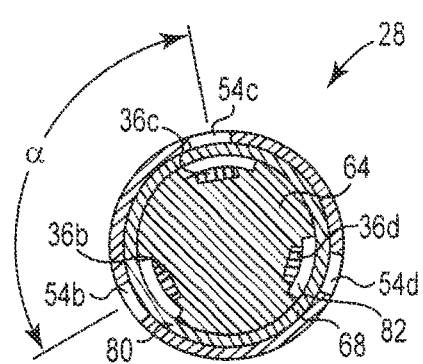
FIG. 5 is a cross-sectional view of the ablation electrode tip along line 5-5 in FIG. 3.

FIG. 5 is a cross-sectional view of the ablation electrode tip 28 along line 5-5 of FIG. 3. As can be further seen in conjunction with FIGS. 4 and 5, a tubular-shaped shell 80 disposed radially about the tip insert body 64 defines an annular-shaped fluid channel 82 connecting the proximal fluid chamber 60 with the distal fluid chamber 62. In other embodiments, the shape of the fluid channel 82 is different from that shown. In some embodiments, the shell 80 comprises an acoustically transparent material such as clear acrylic, which has a relatively low acoustic impedance. The shell 80 also serves to fluidly seal the acoustic openings 54b, 54c, 54d from the surrounding body tissue and, in some embodiments, provides a desired acoustic coupling effect between the cooling fluid within the fluid channel 82 and the body tissue.

As can be further seen in FIG. 5, and in some embodiments, the ablation electrode tip 28 includes three laterally-facing ultrasonic imaging sensors 36b, 36c, 36d at equidistant angles α of 120° about the circumference of the tip 28. Although three laterally-facing ultrasonic imaging sensors 36b, 36c, 36d are shown, a greater or lesser number of sensors may be employed in other embodiments. By way of example and not limitation, four ultrasonic imaging sensors may be disposed at equidistant angles α of 90° about the circumference of the ablation electrode tip 28. In some embodiments, the laterally-facing ultrasonic imaging sensors 36b, 36c, 36d are configured to transmit ultrasonic waves in a direction perpendicular to the side of the ablation electrode tip 28. In other embodiments, the laterally-facing ultrasonic imaging sensors 36b, 36c, 36d are configured to transmit ultrasonic waves from the side of the ablation electrode tip 28 at a slight forward angle.

During imaging, the use of multiple ultrasonic imaging sensors 36b, 36c, 36d spaced about the circumference of the ablation electrode tip 28 ensures that at least one of the laterally-facing sensors 36b, 36b, 36d is in view of target tissue located to the side of the tip 28 irrespective of the tip orientation. Such configuration also permits the physician to easily visualize the target tissue without having to rotate the probe 12 once the probe 12 is in contact with the tissue.

Figure 6:
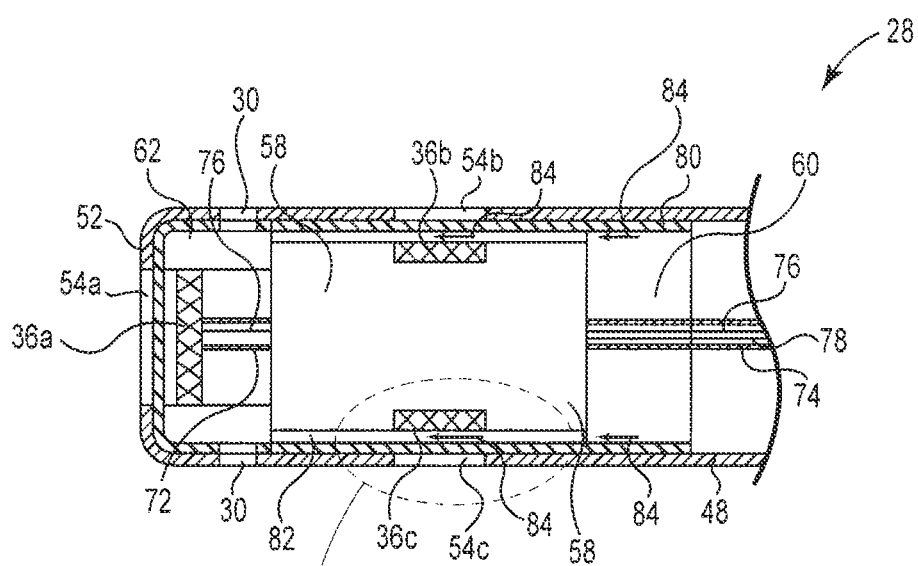
FIG. 6 is another schematic view of the ablation electrode tip showing the flow of cooling fluid across the surface of the ultrasonic imaging sensors.

FIG. 6 is another schematic view of the ablation electrode tip 28 showing the flow of cooling fluid 84 across the surface of the ultrasonic imaging sensors 36b, 36c, 36d. During an ablation procedure, cooling fluid 84 delivered through the probe body 20 enters into the proximal fluid chamber 60. The cooling fluid 84 then enters into the fluid channel 82 and passes across the ultrasonic imaging sensors 36b, 36c, 36d, providing an acoustic coupling effect between the sensors 36b, 36c, 36d and the shell 80. The cooling fluid 84 then enters into the distal fluid chamber 62 and exits into the surrounding body tissue through the irrigation ports 30 shown in FIGS. 1-2.

Figure 7:
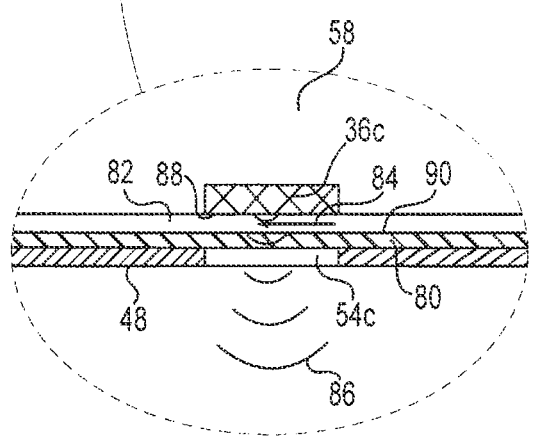
FIG. 7 is an enlarged view showing the transmission of ultrasonic waves from one of the ultrasonic imaging sensors through the cooling fluid, acoustically transparent shell, and acoustic opening of the ablation electrode tip.

FIG. 7 is an enlarged view showing the transmission of ultrasonic waves 86 from one of the ultrasonic imaging sensors 36c through the cooling fluid 84, shell 80, and acoustic opening 54c of the ablation probe tip 28. As shown in FIG. 7, the cooling fluid 84 within the fluid channel 82 comes into contact with the transmitting/receiving surface 88 of the ultrasonic imaging sensor 30c and the interior surface 90 of the shell 80. The cooling fluid 84 is selected so as to have an acoustic impedance similar to that of the body tissue, which serves to facilitate transmission of the ultrasonic waves 86 into the shell 80, through the acoustic opening 54c, and into the tissue within minimal boundary reflection losses at each interface. A similar effect occurs for the fluid passing across the transmitting face or surface for other ultrasonic imaging sensors 36b, 36c.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. An ablation system for treating and imaging body tissue, the system comprising:
   a probe comprising:
      an elongate probe body having a proximal section and a distal section;
      an ablation electrode coupled to the distal section of the elongate probe body, the ablation electrode comprising a conductive shell having an interior, the ablation electrode configured for delivering ablation energy to body tissue;
      a plurality of openings disposed through the ablation electrode;
      a distal insert arranged within the interior of the conductive shell, the distal insert comprising a plurality of recesses;
      a plurality of ultrasonic imaging sensors, wherein each ultrasonic imaging sensor of the plurality of ultrasonic imaging sensors is disposed within a recess of the plurality of recesses of the distal insert;
      an acoustically transparent tubular member disposed between the ultrasonic imaging sensors and the openings; and
      at least one fluid channel, wherein each fluid channel of the at least one fluid channel is interposed between an ultrasonic imaging sensor of the plurality of ultrasonic imaging sensors and an opening of the plurality of openings,
   a fluid source configured for delivering cooling fluid through the at least one fluid channel of the probe, the cooling fluid configured to acoustically couple the ultrasonic imaging sensors to the body tissue;
   a radio frequency generator configured for generating and supplying an electrical ablation energy to the ablation electrode of the probe configured to ablate tissue; and
   a processor configured for processing ultrasonic imaging signals received from the ultrasonic imaging sensors of the probe.

2. The system of claim 1, wherein each ultrasonic imaging sensor is configured to transmit ultrasonic waves through the at least one fluid channel, the acoustically transparent member, and a corresponding one of the openings.

3. The system of claim 1, wherein the conductive shell of the ablation electrode is a tubular metal shell.

4. The system of claim 1, wherein the plurality of openings are located circumferentially about the ablation electrode.

5. The system of claim 1, wherein the acoustically transparent tubular member circumferentially surrounds the plurality of ultrasonic imaging sensors.

6. The system of claim 1, further comprising a graphical user interface, wherein the processor is configured to generate images on the graphical user interface based on the ultrasonic imaging signals and indicative of body tissue sensed by the ultrasonic imaging sensors.

7. The system of claim 1, wherein the ablation electrode includes a proximal fluid chamber and a distal fluid chamber, wherein the proximal and distal fluid chambers are separated by the insert.

8. The system of claim 1, wherein the ablation electrode further includes a plurality of irrigation ports.

9. The system of claim 8, wherein the irrigation ports are in fluid communication with the fluid channel.

10. The system of claim 8, wherein the irrigation ports are located circumferentially about the ablation electrode.

11. The system of claim 8, wherein the irrigation ports are located distally and proximally of the openings.

12. The system of claim 8, wherein the ultrasonic imaging sensors are located within the interior of the conductive shell at a location proximal to the irrigation ports.

13. The system of claim 1, wherein the plurality of ultrasonic imaging sensors are each configured for transmitting laterally-directed ultrasonic waves from a side of the ablation electrode.

14. The system of claim 13, further comprising at least one additional ultrasonic imaging sensor disposed within the interior of the conductive shell, the at least one additional ultrasonic imaging sensor configured for transmitting ultrasonic waves in a distal direction away from a distal end of the ablation electrode.

15. The system of claim 14, wherein the acoustically transparent member is further disposed between the at least one additional ultrasonic imaging sensor and a distal-facing opening disposed through the ablation electrode, and wherein a fluid channel of the at least one fluid channel is further interposed between the at least one additional ultrasonic imaging sensor and the distal-facing opening.

16. The system of claim 1, wherein the insert comprises a cylindrically-shaped insert body.

17. The system of claim 16, wherein a transmitting face of each ultrasonic imaging sensor is substantially flush with an outer surface of the insert body.

* * * * *